(12) United States Patent
Montes

(10) Patent No.: US 7,018,661 B2
(45) Date of Patent: Mar. 28, 2006

(54) ALUMINUM-ZIRCONIUM COMPOUND-BASED TREATMENT FOR HERPES SIMPLEX VIRUS LESIONS

(76) Inventor: Joseph G. Montes, 2711 Whitney Ave., Baltimore, MD (US) 21215

( * ) Notice: Subject to any disclaimer, the term of this patent is extended or adjusted under 35 U.S.C. 154(b) by 88 days.

(21) Appl. No.: 10/382,173

(22) Filed: May 20, 2003

(65) Prior Publication Data

US 2004/0234620 A1    Nov. 25, 2004

(51) Int. Cl.
*A61K 31/28* (2006.01)
*A61K 33/06* (2006.01)
*A61K 33/24* (2006.01)
*A61K 7/34* (2006.01)
*A61P 31/22* (2006.01)

(52) U.S. Cl. .................... 424/617; 424/66; 424/68; 424/682; 514/492; 514/887; 514/934

(58) Field of Classification Search .............. 424/617, 424/682, 66, 68; 514/492, 934, 887
See application file for complete search history.

(56) References Cited

U.S. PATENT DOCUMENTS

| 3,903,258 | A | * | 9/1975 | Siegal ......................... 424/66 |
| 5,728,404 | A | * | 3/1998 | von Rheinbaben et al. .. 424/642 |
| 6,475,501 | B1 | * | 11/2002 | Kelly et al. .................. 424/404 |
| 2003/0215408 | A1 | * | 11/2003 | Dees ............................ 424/66 |

FOREIGN PATENT DOCUMENTS

| WO | 97/27837 | * | 8/1997 |
| WO | 99/34828 | * | 7/1999 |
| WO | 03/103691 | * | 12/2003 |

* cited by examiner

*Primary Examiner*—John Pak

(57) ABSTRACT

Aluminum-zirconium compounds applied topically, usually in a cream, gel, or other base, to lesions caused by any strain or type of Herpes simplex virus in humans and in other animals, will lessen the symptoms of the lesions, speed their healing, and possibly make the recurrence of such lesions less likely.

1 Claim, No Drawings

ALUMINUM-ZIRCONIUM COMPOUND-BASED TREATMENT FOR HERPES SIMPLEX VIRUS LESIONS

BACKGROUND

The applicant, Joseph G. Montes, Ph.D., independently discovered the benefits of the aluminum-zirconium based compounds sixteen years ago. Dr. Montes, a graduate of the Pennsylvania State University in 1983, is a biophysicist (molecular biologist) with postdoctoral training in pharmacology (Medical College of Virginia and University of Maryland School of Medicine) and previous experience (including publications) researching Herpes simplex.

One possible mechanism of action for the compounds mentioned herein is dehydration, as the compounds are among the most successful of antiperspirants on the market and Herpes simplex seems to not thrive under dry conditions. However, given the observations made on preliminary trials, it is possible that the aluminum-zirconium compounds also inhibit or retard the recurrence of herpetic lesions, as the three subjects in the trials experienced reduction in the frequency of recurrence of herpetic lesions with each subsequent treatment. There is some support in the literature for the hypothesis that aluminum-zirconium compounds boost the immune response in some localized way (not tested previously by others on herpetic lesions, however), by working at the site of application, perhaps as immune adjuvants (see J Am Acad Dermatol, 37(3 Pt 1): 496–8, 1997).

BRIEF DESCRIPTION OF THE INVENTION

A preparation consisting of one or more of several possible aluminum zirconium compounds is applied in a cream, ointment, gel, or other base to superficial herpetic lesions, causing them to regress markedly and abruptly, relieving the subject of the symptoms, spread, and other manifestations of the herpetic condition.

DETAILED DESCRIPTION OF THE INVENTION

Any one or any combination of aluminum-zirconium compounds, e.g., aluminum-zirconium tetrachlorohydrex glycine, aluminum-zirconium trichlorohydrex glycine, and aluminum-zirconium pentachlorohydrate glycine, as well as other salts and complexes of aluminum-zirconium thereof, are applied topically to herpetic lesions to treat them. One or more of the compounds, usually contained in a cream, ointment, gel, or other base, is applied superficially to herpetic lesions on external skin (such as in the case of "cold sores") or mucous membrane surfaces (such as the vaginal surface, the inside lining of the mouth, and the glans of the penis) at concentrations of 1% to 100%, coating the lesions and surrounding skin or mucous membranes. The substance must not be rubbed off for at least one hour after application and should be applied every 6–8 hours for maximum effect. If caught early, most cases require application of the substance for only two days. The compound(s) may be delivered in a cream, ointment, or gel formulation whose exact composition is not critical to the efficacy of the compound. One such preparation consists of aluminum-zirconium tetrachlorohydrex glycine at a concentration of 18.3% in a gel base consisting of water, denatured alcohol, dimethicone, propylene glycol, cyclomethicone, and dimethicone copolyol. This particular preparation, available over the counter as one of numerous antiperspirants, has been successfully tested on three subjects with recurrent herpetic lesions, producing very dramatic alleviation of discomfort within six to twelve hours or less as well as rapid healing of the lesion(s). In some instances aluminum-zirconium compounds will also retard the spread of the lesions to other parts of the body.

What is clamied is:

1. A method of treating herpetic lesions consisting of the topical administration of an effective amount of one or more aluminum-zirconium compounds to a herpetic lesion on a human patient.

* * * * *